(12) United States Patent
Terren et al.

(10) Patent No.: US 7,083,800 B1
(45) Date of Patent: Aug. 1, 2006

(54) USE OF A SILICONE SURFACTANT OF ALKYL-DIMETHICONE COPOLYOL TYPE FOR PREPARING SOLID WATER-IN-OIL COSMETIC EMULSIONS AND RESULTING SOLID WATER-IN-OIL EMULSIONS

(75) Inventors: Nadia Terren, Bourg-la-Reine (FR); Marie-Martine Roux, Athis-Mons (FR); Sophie Favre, Chevilly-Larue (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/423,974

(22) PCT Filed: Mar. 17, 1999

(86) PCT No.: PCT/FR99/00609

§ 371 (c)(1),
(2), (4) Date: Jan. 5, 2000

(87) PCT Pub. No.: WO99/47111

PCT Pub. Date: Sep. 23, 1999

(30) Foreign Application Priority Data

Mar. 17, 1998 (FR) .................... 98 03250

(51) Int. Cl.
*A61K 7/00* (2006.01)
*A61K 7/021* (2006.01)

(52) U.S. Cl. .................... 424/401; 424/62; 424/63; 424/59; 424/70.1

(58) Field of Classification Search ........... 424/401, 424/70.12, 63, 64; 514/938; 516/23
See application file for complete search history.

(56) References Cited

U.S. PATENT DOCUMENTS

| | | | |
|---|---|---|---|
| 4,536,405 A * | 8/1985 | Nara et al. ............ 424/61 |
| 5,061,481 A | 10/1991 | Suzuki et al. ......... 424/63 |
| 5,196,187 A * | 3/1993 | Nicoll et al. .......... 424/70 |
| 5,456,906 A | 10/1995 | Powell et al. ......... 424/66 |
| 5,650,139 A * | 7/1997 | Nojima ................ 424/64 |
| 5,747,013 A | 5/1998 | Mougin et al. ....... 424/707 |
| 5,851,539 A * | 12/1998 | Mellul et al. ......... 424/401 |
| 5,863,544 A | 1/1999 | Willcox et al. ........ 424/401 |

FOREIGN PATENT DOCUMENTS

| | | |
|---|---|---|
| EP | 0 374 332 | 6/1990 |
| EP | 0 595 683 | 5/1994 |
| JP | 3-72942 | 3/1991 |
| JP | 03-261707 | 11/1991 |
| JP | 11-228343 | 8/1999 |

OTHER PUBLICATIONS

Duane G. Krzysik et al., "A New Silicone Emulsfier For Water-in-Oil Systems", Drug & Cosmetic Industry, vol. 146, No. 9, Apr. 1990.
F. Battioni, "Dalle emulsioni A/O alle emulsioni A/S e viceversa", Il Prodotto Chimico, vol. 28, No. 3, 1987, pp. 32-34.
English language Derwent Abstract of EP 0 595 683.
English language abstract of JP 03-261707.

* cited by examiner

*Primary Examiner*—Sreeni Padmanabhan
*Assistant Examiner*—Gina C. Yu
(74) *Attorney, Agent, or Firm*—Finnegan, Henderson, Farabow, Garrett & Dunner, L.L.P.

(57) ABSTRACT

The present invention relates to the use of a silicone surfactant of alkyl dimethicone copolyol type of formula:

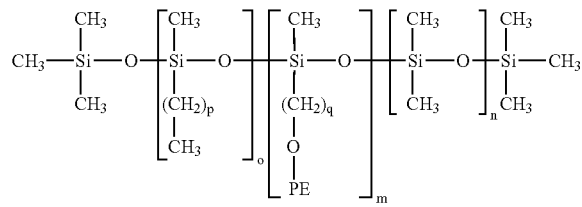

in which:
$PE=(-C_2H_4O)_x(-C_3H_6O)_y-H$,
$x=0$ to 50,
$y=0$ to 30, x and y not simultaneously being 0,
$o=1$ to 100,
$m=1$ to 40,
$n=1$ to 200,
$p=1$ to 17 and
$q=1$ to 5,
in the preparation of a solid water-in-oil emulsion comprising an aqueous phase emulsified by the said surfactant in a fatty phase comprising at least one oil and at least one wax.

The invention also relates to a solid emulsion of water-in-oil type, in particular a transfer-free foundation, such as the emulsion defined above.

34 Claims, No Drawings

USE OF A SILICONE SURFACTANT OF ALKYL-DIMETHICONE COPOLYOL TYPE FOR PREPARING SOLID WATER-IN-OIL COSMETIC EMULSIONS AND RESULTING SOLID WATER-IN-OIL EMULSIONS

The present invention relates to the use of a silicone surfactant of the alkyl dimethicone copolyol type in the preparation of solid cosmetic water-in-oil emulsions and to solid cosmetic water-in-oil emulsions, in particular foundations.

Water-in-oil (W/O) emulsions are commonly used in the cosmetics field as they make it possible to form a film at the surface of the skin which prevents transepidermal water loss and protects the skin from external attacks.

In view of the requirements of consumers with regard to emulsions of this type, which must simultaneously have a good cosmetic quality, which is reflected in terms of appearance, of texture, of ease of application and of good protective properties, good hold and good resistance to sweat and to sebum, it is highly advantageous to be able to obtain emulsions exhibiting all these properties without exhibiting the disadvantages of conventional W/O emulsions.

Solid emulsions of the foundation type generally comprise fatty substances, such as solid waxes and oils, water and a particulate phase generally composed of fillers and pigments.

However, these compositions, when they are applied to the skin, exhibit the disadvantage of transferring, that is to say of being at least partly deposited, while leaving a trace, on certain substrates with which they can be brought into contact, in particular an item of clothing or the skin. This results in mediocre persistence of the film on the skin, requiring the regular renewal of the application of the foundation composition.

Another disadvantage of the compositions of the prior art is poor dispersion of the pigments, resulting in an emulsion which is not homogeneous.

Patent Application JP-A-03261707 discloses solid cosmetic compositions of the water-in-oil emulsion type comprising silicone oils, solid waxes and water which also comprise spherical powders.

The emulsifiers used can be organopolysiloxanes modified by polyoxyalkylenes, such as dimethicone copolyols.

The solid emulsions obtained, namely foundations, are nonhomogeneous and coarse and have a microscopic appearance which does not conform and a macroscopic appearance which does not conform, and the pigments are not well dispersed.

The aim of the present invention is to overcome these disadvantages and the invention provides a solid homogeneous W/O emulsion, in which the pigments, dyes and oils are well dispersed, which is soft, which has good slip, which has very good hold and which has good persistence on the skin.

The Applicant Company has discovered, surprisingly and unexpectedly, that it is possible, by using a specific silicone surfactant of the alkyl dimethicone copolyol type, in combination with at least one oil and at least one wax, to obtain a solid water-in-oil emulsion which exhibits the desired characteristics and which also exhibits the advantage of not transferring.

The subject-matter of the invention is therefore the use of a silicone surfactant of the alkyl dimethicone copolyol type, the formula of which is shown hereinbelow, in the preparation of solid emulsions of the water-in-oil type comprising an aqueous phase emulsified by the said surfactant in a fatty phase comprising at least one oil and at least one wax.

Another subject-matter of the invention is a solid cosmetic water-in-oil emulsion, characterized in that it comprises an aqueous phase emulsified, using a silicone surfactant of the alkyl dimethicone copolyol type with the formula shown hereinbelow, in a fatty phase comprising at least one oil and at least one wax.

Another subject-matter of the invention is a process for making up the skin and/or scalp, characterized in that a solid emulsion as defined above is applied to the skin and/or to the scalp.

The Applicant Company has found that the solid emulsion according to the invention is applied and is spread easily in a homogeneous way and exhibits good moisturizing properties and good cosmetic properties since it is soft and has good slip. The film obtained also exhibits a light texture and remains comfortable to wear throughout the day.

Furthermore, the emulsion applied to the skin exhibits the advantage of not migrating into the folds of the skin and/or the wrinkles of the face.

The emulsion according to the invention exhibits a homogeneous texture. Additives can be added to the emulsion according to the invention while retaining a stable emulsion. The emulsion according to the invention is therefore compatible with a large number of cosmetic adjuvants.

The silicone surfactant of the alkyl dimethicone copolyol type used according to the invention has the formula:

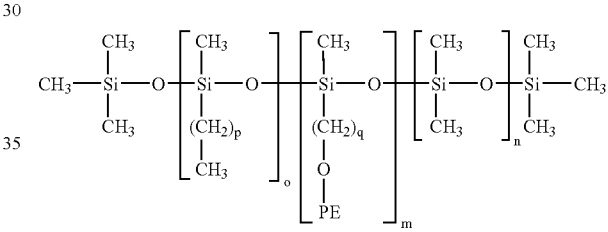

in which:

$PE = (-C_2H_4O)_x(-C_3H_6O)_y-H$, $x = 0$ to $50$, $y = 0$ to $30$, x and y not simultaneously being 0, $o = 1$ to $100$, $m = 1$ to $40$, $n = 1$ to $200$, $p = 1$ to $17$ and $q = 1$ to $5$, and preferably, $o = 1$ to $25$, $m = 1$ to $10$, $n = 1$ to $100$.

Such silicone surfactants are commercial products and mention may be made, as examples, of the compounds sold under the names:

"Abil WE 09" by the Company Goldschmidt, which corresponds to the above formula and in which:

$o = 21$, $m = 4$ n=73,

"Abil WS 08" and "Abil EM 90" by the Company Goldschmidt,

"218-1138" by the Company General Electric, which corresponds to the above formula and in which

PE=$(C_2H_4O)_{12}$—H o=2 m=8 n=20 p=9 q=3.

Use is preferably made of the product "Abil WE 09", which is a mixture of cetyl dimethicone copolyol (CTFA name), of polyglyceryl-4 isostearate and of hexyl laurate (33.3%/33.3%/33.4%).

The silicone surfactant, alkyl dimethicone copolyol, is used in a proportion of 0.5 to 40% by weight on the basis of the total weight of the emulsion and preferably in a proportion of 2 to 12% by weight.

The fatty phase of the solid emulsion according to the invention comprises at least one oil and at least one wax.

The emulsion according to the invention advantageously comprises 10 to 40% by weight and preferably 18 to 30% by weight, with respect to the total weight of the emulsion, of at least one oil.

The emulsion according to the invention preferably comprises at least one silicone oil.

Mention may be made, as examples of silicone oils used in the invention, of:

volatile cyclic silicones having from 3 to 8 silicon atoms and preferably 4 to 6, such as, for example, cyclotetradimethylsiloxane, cyclopentadimethylsiloxane or cyclohexadimethylsiloxane;

cyclocopolymers of the dimethylsiloxane/methylalkylsiloxane type, such as "silicone FZ 3109" sold by the Company Union Carbide, which is a dimethylsiloxane/methyloctylsiloxane cyclocopolymer;

volatile linear silicones having from 2 to 9 silicon atoms, for example hexamethyldisiloxane, hexylheptamethyltrisiloxane and octylheptamethyltrisiloxane;

polyalkylsiloxanes with trimethylsilyl end groups, preferably those for which the viscosity at 25° C. is less than or equal to 0.06 m²/s, among which may be mentioned linear polydimethylsiloxanes, in particular those sold under the name "Dow Corning Fluid 200" by the Company Dow Corning, and alkylmethylpolysiloxanes, such as cetyl dimethicone (CTFA name);

phenylated silicone oils.

Volatile silicone oils are preferred for use in the invention.

Mention may also be made, as volatile oils preferably used according to the invention, of hydrocarbon-comprising oils having from 8 to 16 carbon atoms and in particular volatile $C_8$–$C_{16}$ isoparaffin oils, such as isododecane, isodecane and isohexadecane.

The emulsion according to the invention can also comprise other oils and pasty fatty substances.

Pasty fatty compounds can be defined using at least one of the following physicochemical properties:

a viscosity of 0.1 to 40 Pa·s, preferably 0.5 to 25 Pa·s, measured at 40° C. with a Contraves TV rotary viscometer equipped with an MS-r3 or MS-r4 rotor at a frequency of 60 Hz, a melting point of 25–70° C., preferably 25–55° C.

Mention may be made, among the other oils which can be used according to the invention, of:

mineral oils, such as liquid paraffin or liquid petrolatum, animal oils, such as perhydrosqualene, vegetable oils, such as apricot oil, sesame oil, sweet almond oil, calophyllum oil, palm oil, castor oil, avocado oil, jojoba oil, olive oil or cereal germ oil, such as wheat germ oil, branched $C_8$–$C_{16}$ esters, such as isohexyl neopentanoate, synthetic esters and ethers, such as oils of formula $R_1COOR_2$ in which $R_1$, represents the residue of a higher fatty acid comprising from 6 to 29 carbon atoms and $R_2$ represents a hydrocarbon-comprising chain comprising from 3 to 30 carbon atoms, such as purcellin oil, isopropyl myristate, 2-ethylhexyl palmitate, 2-octyldodecyl stearate, 2-octyldodecyl erucate, isostearyl isostearate, arachidyl propionate or 2-octyldodecyl benzoate; hydroxylated esters, such as isostearyl lactate, octyl hydroxystearate, octyldodecyl hydroxystearate, diisostearyl malate or triisocetyl citrate; or polyol esters, such as propylene glycol dioctanoate, neopentyl glycol diheptanoate, diethylene glycol diisononanoate and pentaerythritol esters;

fatty alcohols having from 12 to 16 carbon atoms, such as octyldodecanol, 2-butyloctanol, 2-hexyldecanol, 2-undecylpentadecanol or oleyl alcohol;

fluorinated oils, among which may be mentioned perfluoropolyethers, such as the products sold under the trade name "Fomblin" by the Company Montefluos, and fluorinated silicones, such as trifluoromethyl ($C_1$–$C_4$)alkyl dimethicones, for example that sold under the trade name "X 22819" by the Company Shin Etsu; and their mixtures.

The cosmetic emulsion according to the invention advantageously also comprises 3 to 15% by weight and preferably 3 to 10% by weight, on the basis of the total weight of the emulsion, of at least one vegetable, mineral, animal and/or synthetic wax.

Mention may be made, as waxes which can be used according to the invention, of waxes of animal origin, such as beeswax, spermaceti, lanolin wax and lanolin derivatives, vegetable waxes, such as carnauba, candelilla, ouricury or japan wax, cocoa butter or cork fibre or sugar cane waxes, mineral waxes, for example paraffin wax, petrolatum wax, lignite wax or microcrystalline waxes or ozokerites, synthetic waxes, including polyethylene or polytetrafluoroethylene waxes and waxes obtained by the Fischer-Tropsch synthesis, or alternatively silicone waxes, hydrogenated oils which are solid at 25° C., such as hydrogenated castor oil, hydrogenated jojoba oil, hydrogenated palm oil, hydrogenated tallow or hydrogenated coconut oil, and fatty esters which are solid at 25° C., such as the $C_{20}$–$C_{40}$ alkyl stearate sold under the trade name "Kester Wax K82H" by the Company Koster Keunen.

The silicone waxes which can be used in the composition according to the invention can be substituted linear polysiloxanes. Mention may be made, for example, of silicone polyether waxes or alkyl or alkoxy dimethicones having from 16 to 45 carbon atoms. Mention may also be made of alkyl methicones, such as the $C_{30}$–$C_{45}$ alkyl methicone sold under the trade name "AMS C 30" by Dow Corning.

Use is preferably made of a wax or a mixture of waxes capable of conferring, on the solid emulsion according to the invention, a penetration force of greater than or equal to 50 grams (g).

In the present application, this penetration force is measured according to the following protocol: after preparation of the emulsion, the latter is cast in a dish and is maintained at 20° C. for 24 hours. The penetration force is then measured on this solid emulsion using a Stevens texture-analysing device with the TA24 measurement rotor, with a diameter of 4 mm, at a penetration rate of 0.5 mm/s and at a preselected penetration depth of 2 mm. The penetration force, expressed in grams, is read on the device.

Use is preferably made of a wax chosen from polyethylene wax, hydrogenated jojoba oil, ozokerite or their mixtures.

More preferably, the emulsion according to the invention comprises polyethylene wax. More preferably still, the emulsion according to the invention comprises a mixture of polyethylene wax and of hydrogenated jojoba oil.

The aqueous phase of the emulsion according to the invention can represent 0.5 to 60% by weight of the total weight of the emulsion.

It can comprise water or a floral water, such as cornflower water.

The aqueous phase according to the invention can comprise 0 to 14% by weight of lower $C_2$–$C_6$ monoalcohols and/or of polyols, such as glycerol, butylene glycol, isoprene glycol and propylene glycol, and agents for the stabilization of the emulsion, for example sodium chloride, magnesium dichloride and magnesium sulphate.

In addition, the emulsion according to the invention can comprise one or more thickening agents in concentrations preferably ranging from 0 to 6% by weight with respect to the total weight of the emulsion.

The emulsion according to the invention can also comprise a particulate phase which can comprise pigments and/or pearlescent agents and/or fillers commonly used in the field of cosmetics and make-up. A person skilled in the art will take care, however, to select these compounds for minimum transfer.

The pigments can be present in the emulsion in a proportion of 0 to 30% by weight with respect to the total weight of the emulsion and preferably in a proportion of 2 to 20%. They can be white or coloured and inorganic and/or organic and have a conventional or nanometric size. Mention may be made, among inorganic pigments and nanopigments, of titanium, zirconium or cerium dioxides, as well as zinc, iron or chromium oxides, nano-sized titanium oxides and ferric blue. Mention may be made, among organic pigments, of carbon black, barium, strontium, calcium and aluminium lakes, and cochineal carmine.

The term "fillers" should be understood as meaning colourless or white, inorganic or synthetic, lamellar or nonlamellar particles. The term "pearlescent agents" should be understood as meaning iridescent particles, produced in particular by certain molluscs in their shells or else synthesized. These fillers and pearlescent agents are used in particular to modify the texture of the composition.

The fillers can be present in the emulsion in a proportion of 0 to 25% by weight with respect to the total weight of the emulsion, preferably 0 to 10%. Mention may in particular be made of talc, mica, silica, kaolin, Teflon, starch, boron nitride, Nylon powder (in particular Orgasol), polyethylene powder, copolymer microspheres, such as Expancel (Nobel Industrie) or Polytrap (Dow Corning), and silicone resin microbeads (Tospearl from Toshiba, for example).

The pearlescent agents can be present in the emulsion in a proportion of 0 to 20% by weight with respect to the total weight of the emulsion, preferably of 2 to 15%.

The pearlescent agents which can be used according to the invention are, for example, mica covered with titanium oxide, with iron oxide, with natural pigment or with bismuth oxychloride, as well as coloured titanium oxide-coated mica.

The emulsion according to the invention can additionally comprise any additive conventionally used in the cosmetics field, such as antioxidants, colorants, fragrances, essential oils, preservatives, cosmetic active principles, moisturizers, vitamins, sphingolipids, sunscreen agents or fat-soluble polymers, in particular hydrocarbon-comprising polymers, such as polybutene, polyalkylenes, polyacrylates and silicone polymers compatible with fatty substances. Of course, a person skilled in the art will take care to choose this or these optional additional compounds and/or their amount so that the advantageous properties of the composition according to the invention are not, or not substantially, detrimentally affected by the envisaged addition. These additives can be present in the composition in a proportion of 0 to 15% by weight.

The emulsions according to the invention can be provided in the form of a cosmetic product and in particular in the form of a make-up product, in particular a foundation, a face powder, an eyeshadow or a lipstick.

They can also be provided in the uncoloured form, optionally comprising cosmetic active principles.

The examples which follow serve to illustrate the invention without, however, exhibiting a limiting nature. In these examples, the amounts are given as percentage by weight with respect to the total weight of the composition.

EXAMPLE 1

The Applicant Company has prepared the following foundation:

| PHASE O | |
|---|---|
| Hydrogenated jojoba oil | 5.6% |
| Preservative | 0.3% |
| Polyethylene wax (MW: 500) | 2.9% |
| Polytetrafluoroethylene wax | 7% |
| Mixture of oxyethylenated and oxypropylenated poly(methylcetyl) (dimethyl) (methylsiloxane), polyglycerolated isostearate (4 mol) and hexyl laurate, sold under the name "Abil WE 09" by the Company Goldschmidt | 9% |
| SILICONE S | |
| Cyclohexadimethylsiloxane (viscosity: $8 \times 10^{-6}$ m$^2$/s) | 24.3% |
| PIGMENTS P | |
| Iron oxides | 2.9% |
| Titanium oxide | 7.1% |
| PHASE W | |
| Sterilized demineralized water | 38.5% |
| Propylene glycol | 1% |
| Preservative | 0.4% |
| Magnesium sulphate.7H$_2$O | 1% |

The compounds of the phase O are weighed together and are heated to 100° C.

After homogenization, the phase is cooled to 80° C. and then the silicone S is added.

The pigments P are subsequently dispersed in the O+S mixture.

After homogenization, the phase W, preheated to 80° C., is slowly added while stirring using a Moritz-type stirrer and while retaining, during the addition, a minimum temperature of 75° C.

The product is cast and a homogeneous compact foundation is obtained which spreads well, which results in a highly natural and very soft make-up, which exhibits good cosmetic hold and which does not transfer.

This composition has a penetration force, measured on a Stevens device as described in the above text, of greater than 50 grams.

EXAMPLE 2

Comparative: Foundation According to the Prior Art

Example 5 of Application JP-A-03261707 was repeated.

| PHASE O | |
|---|---|
| Paraffin wax (mineral wax) | 4% |
| Dimethicone copolyol, cyclopentasiloxane and water (10/88/2) mixture, sold under the name "Q2-3225 C" by the Company Dow Corning | 30% |
| Camphor | 0.1% |
| Menthol | 0.1% |
| Microcrystalline cellulose | 3% |
| PIGMENTS P | |
| Titanium dioxide coated with polydimethylsiloxane | 15% |
| Yellow iron oxide coated with polydimethylsiloxane | 3% |
| Red iron oxide coated with polydimethylsiloxane | 1% |
| Black iron oxide coated with polydimethylsiloxane | 0.2% |
| PHASE W | |
| Water | 33% |
| Ethanol | 5% |
| Polyethylene glycol | 5% |
| Methyl p-hydroxybenzoate | 0.3% |

A compact foundation is prepared according to the above procedure.

A foundation is obtained which is heterogeneous in colour, which is nonhomogeneous, which has pigments which are badly dispersed and which is rough and dry on application.

EXAMPLE 3

The Applicant Company has prepared the following three compositions A, B and C, the nature of the wax being varied:

| PHASE O | |
|---|---|
| Wax | 6.3% |
| Preservative | 0.3% |
| Mixture of oxyethylenated and oxypropylenated poly(methylcetyl) (dimethyl) (methylsiloxane), polyglycerolated isostearate (4 mol) and hexyl laurate, sold under the name "Abil WE 09" by the Company Goldschmidt | 9% |
| SILICONE S | |
| Cyclohexadimethylsiloxane (viscosity: 8 × 10$^{-6}$ m$^2$/s) | 24.3% |
| PIGMENTS P | |
| Iron oxides | 2.9% |
| Titanium oxide | 7.1% |
| PHASE W | |

| -continued | |
|---|---|
| Sterilized demineralized water | 38.5% |
| Propylene glycol | 1% |
| Preservative | 0.4% |
| Magnesium sulphate.7H$_2$O | 1% | with:

| Composition | A | B | C |
|---|---|---|---|
| Nature of the wax | Hydrogenated jojoba oil | Polyethylene | Carnauba |
| Penetration force (in g) | 74 | 101 | 11 |
| Appearance after hot casting | Non-smooth solid | Solid | Soft |
| Observation under a microscope | Fine but not very even emulsion | Fine, even emulsion | Small crystals |

These three emulsions were prepared as in Example 1. The penetration force was measured on a Stevens device as described in the above text.

The emulsion C, which only comprises carnauba wax, does not make it possible to obtain a sufficiently solid composition.

The invention claimed is:

1. A solid cosmetic water-in-oil emulsion comprising an aqueous phase emulsified in a fatty phase comprising at least one oil and at least one wax, wherein the aqueous phase is emulsified using an alkyl dimethicone copolyol corresponding to the following formula:

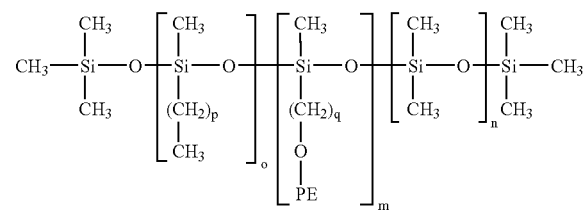

in which:
PE is $(-C_2H_4O)_x(-C_3H_6O)_y-H$,
x ranges from 0 to 50,
y ranges from 0 to 30, with the proviso that x and y are not simultaneously 0,
o ranges from 1 to 100,
m ranges from 1 to 40,
n ranges from 1 to 200,
p ranges from 1 to 17, and
q ranges from 1 to 5, and
further wherein the at least one wax in the fatty phase is capable of conferring a penetration force on the emulsion of greater than or equal to 50 grams;
further wherein the at least one oil in the fatty phase comprises a silicone oil, and the at least one wax is chosen from polyethylene wax, hydrogenated jojoba oil, and ozokerite.

2. The emulsion according to claim 1, wherein
o ranges from 1 to 25,
m ranges from 1 to 10, and
n ranges from 1 to 100.

3. The emulsion according to claim 2, wherein
o is 21,
m is 4, and
n is 73.

4. The emulsion according to claim 1, wherein the alkyl dimethicone copolyol is a mixture of cetyl dimethicone copolyol, polyglyceryl-4 isostearate and hexyl laurate.

5. The emulsion according to claim 1, wherein the alkyl dimethicone copolyol is present in said emulsion in an amount of from 0.5 to 40% by weight with respect to the total weight of the emulsion.

6. The emulsion according to claim 5, wherein the alkyl dimethicone copolyol is present in said emulsion in an amount of from 2 to 12% by weight with respect to the total weight of the emulsion.

7. The emulsion according to claim 1, wherein the at least one oil in the fatty phase is a silicone oil.

8. The emulsion according to claim 1, wherein the silicone oil is chosen from volatile cyclic silicones having from 3 to 8 silicon atoms, volatile linear silicones having from 2 to 9 silicon atoms, dimethylsiloxane/methylalkylsiloxane cyclocopolymers, polyalkylsiloxanes with trimethylsilyl end groups, and phenylated silicone oils.

9. The emulsion according to claim 8, wherein the silicone oil is a volatile cyclic silicone having from 3 to 8 silicon atoms.

10. The emulsion according to claim 9, wherein the volatile cyclic silicone having from 3 to 8 silicon atoms is chosen from cyclotetradimethylsiloxane, cyclopentadimethylsiloxane, and cyclohexadimethylsiloxane.

11. The emulsion according to claim 8, wherein the silicone oil is a volatile linear silicone having from 2 to 9 silicon atoms.

12. The emulsion according to claim 11, wherein the silicone oil is a volatile linear silicone having from 2 to 9 silicon atoms is chosen from hexamethyldisiloxane, hexylheptamethyltrisiloxane, and octylheptamethyltrisiloxane.

13. The emulsion according to claim 1, wherein the at least one oil in the fatty phase further comprises a volatile isoparaffin.

14. The emulsion according to claim 13, wherein the volatile isoparaffin is a $C_8$–$C_{16}$ isoparaffin.

15. The emulsion according to claim 14, wherein the $C_8$–$C_{16}$ isoparaffin is chosen from isododecane, isodecane, and isohexadecane.

16. The emulsion according to claim 1, wherein the fatty phase further comprises at least one additional component chosen from mineral oils, oils of animal origin, vegetable oils, branched $C_8$–$C_{16}$ esters, synthetic esters and ethers, hydroxylated esters, polyol esters, fatty alcohols, and fluorinated oils.

17. The emulsion according to claim 1, wherein the fatty phase further comprises at least one additional ingredient chosen from pigments, pearlescent agents, and fillers, and further wherein the at least one additional ingredient is selected so as not to affect any transfer-resistant properties of said emulsion.

18. The emulsion according to claim 1, wherein the at least one oil is present in said emulsion in an amount of from 10 to 40% by weight with respect to the total weight of the emulsion.

19. The emulsion according to claim 18, wherein the at least one oil is present in said emulsion in an amount of from 18 to 30% by weight with respect to the total weight of the emulsion.

20. The emulsion according to claim 1, wherein the at least one wax is chosen from vegetable, mineral, animal and synthetic waxes, hydrogenated oils that are solid at 25° C., and fatty esters that are solid at 25° C.

21. The emulsion according to claim 20, wherein the at least one wax is chosen from polyethylene wax, hydrogenated jojoba oil, and ozokerite.

22. The emulsion according to claim 1, wherein the at least one wax is a mixture of polyethylene wax and of hydrogenated jojoba oil.

23. The emulsion according to claim 1, wherein the at least one wax is present in said emulsion in an amount of from 3 to 15% by weight with respect to the total weight of the emulsion.

24. The emulsion according to claim 23, wherein the at least one wax is present in said emulsion in an amount of from 3 to 10% by weight with respect to the total weight of the emulsion.

25. The emulsion according to claim 1, wherein the aqueous phase is present in said emulsion in an amount of from 0.5 to 60% of the total weight of the emulsion.

26. The emulsion according to claim 1, wherein the aqueous phase comprises
a) water or a floral water;
b) 0 to 14% by weight, with respect to the total weight of the aqueous phase, of lower $C_2$–$C_6$ monoalcohols and/or of polyols; and
c) 0 to 6% by weight, with respect to the total weight of the emulsion, of a thickening agent.

27. The emulsion according to claim 26, wherein the aqueous phase further comprises agents for stabilization of the emulsion.

28. The emulsion according to claim 1, wherein it additionally comprises at least one additive chosen from antioxidants, colorants, fragrances, essential oils, preservatives, cosmetic active principles, moisturizers, vitamins, sphingolipids, sunscreen agents, and fat-soluble polymers.

29. The emulsion according to claim 1, wherein the emulsion is a solid, transfer-free compact foundation.

30. A process for making up the skin and/or scalp, comprising applying to the skin and/or the scalp, a solid cosmetic water-in-oil emulsion comprising an aqueous phase emulsified in a fatty phase comprising at least one oil and at least one wax, wherein the aqueous phase is emulsified using an alkyl dimethicone copolyol corresponding to the following formula:

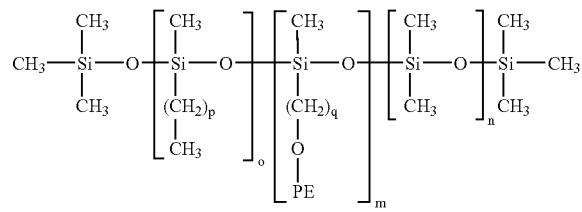

in which:
PE is (—$C_2H_4O$)$_x$(—$C_3H_6O$)$_y$—H,
x ranges from 0 to 50,
y ranges from 0 to 30, with the proviso that x and y are not simultaneously 0,
o ranges from 1 to 100,
m ranges from 1 to 40,
n ranges from 1 to 200,
p ranges from 1 to 17, and
q ranges from 1 to 5, and further wherein the at least one wax in the fatty phase is capable of conferring a penetration force on the emulsion of greater than or equal to 50 grams;

further wherein the at least one oil in the fatty phase comprises a silicone oil, and the at least one wax is chosen from polyethylene wax, hydrogenated jojoba oil, and ozokerite.

31. The process according to claim 30, wherein
o ranges from 1 to 25,
m ranges from 1 to 10, and
n ranges from 1 to 100.

32. The process according to claim 31, wherein
o is 21,
m is 4, and
n is 73.

33. A transfer-resistant cosmetic composition comprising a solid cosmetic water-in-oil emulsion comprising an aqueous phase emulsified in a fatty phase comprising at least one oil and at least one wax, wherein the aqueous phase is emulsified using an alkyl dimethicone copolyol corresponding to the following formula:

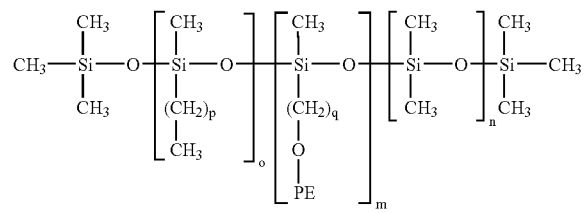

in which:
PE is $(-C_2H_4O)_x(-C_3H_6O)_y-H$,
x ranges from 0 to 50,
y ranges from 0 to 30, with the proviso that x and y are not simultaneously 0,
o ranges from 1 to 100,
m ranges from 1 to 40,
n ranges from 1 to 200,
p ranges from 1 to 17, and
q ranges from 1 to 5, and
further wherein the at least one wax in the fatty phase is capable of conferring a penetration force on the emulsion of greater than or equal to 50 grams;
and wherein the solid water-in-oil emulsion is present in the composition in an amount effective to provide transfer-resistant properties to the composition.

34. A method for providing transfer-resistant properties to a cosmetic composition, said process comprising including in said composition a solid cosmetic water-in-oil emulsion comprising an aqueous phase emulsified in a fatty phase comprising at least one oil and at least one wax, wherein the aqueous phase is emulsified using an alkyl dimethicone copolyol corresponding to the following formula:

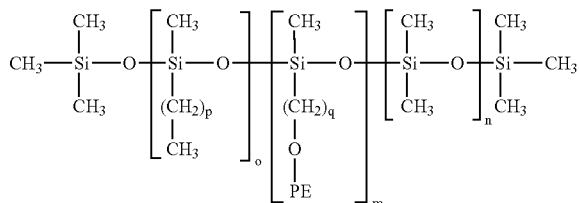

in which:
PE is $(-C_2H_4O)_x(-C_3H_6O)_y-H$,
x ranges from 0 to 50,
y ranges from 0 to 30, with the proviso that x and y are not simultaneously 0,
o ranges from 1 to 100,
m ranges from 1 to 40,
n ranges from 1 to 200,
p ranges from 1 to 17, and
q ranges from 1 to 5, and
further wherein the at least one wax in the fatty phase is capable of conferring a penetration force on the emulsion of greater than or equal to 50 grams.

* * * * *